United States Patent [19]

Kende et al.

[11] 4,122,092
[45] Oct. 24, 1978

[54] TOTAL SYNTHESIS OF (±)-PICROPODOPHYLLONE AND (±)-4'-DEMETHYLPICROPODOPHYLLONE

[75] Inventors: Andrew S. Kende, Pittsford; Peter S. Rutledge, Rochester, both of N.Y.

[73] Assignee: University of Rochester, Rochester, N.Y.

[21] Appl. No.: 827,487

[22] Filed: Aug. 25, 1977

[51] Int. Cl.$^2$ ............................................ C07D 317/44
[52] U.S. Cl. ........................ 260/340.5 R; 260/239 A; 260/343.3 R
[58] Field of Search .............................. 260/340.5 OD

[56] References Cited

U.S. PATENT DOCUMENTS 4,059,593  11/1977  Kende et al. .................. 260/340.5 R

FOREIGN PATENT DOCUMENTS 1,088,621  10/1967  United Kingdom .................. 260/340.5

OTHER PUBLICATIONS

Gensler et al., Journ. Amer. Chem. Soc. 82, pp. 1714–1727 (1960).

Primary Examiner—Ethel G. Love
Attorney, Agent, or Firm—Richard R. Lloyd

[57] ABSTRACT

Efficient total syntheses of (±)-picropodophyllone and (±)-4'-demethylpicropodophyllone are described. These compounds are intermediates in the preparation of known antineoplastic agents.

7 Claims, No Drawings

TOTAL SYNTHESIS OF (±)-PICROPODOPHYLLONE AND (±)-4'-DEMETHYLPICROPODOPHYLLONE

The invention described herein was made in the course of Grant No. CA-18846 from the National Cancer Institute, Department of Health, Education and Welfare.

SUMMARY OF THE DISCLOSURE

This invention relates to the preparation of podophyllin lignan lactones and 4'-demethylpodophyllin lignan lactones. More specifically, this invention relates to new and efficient total syntheses of (±)-picropodophyllone (I) and (±)-4'-demethylpicropodophyllone (II), which are readily converted by known procedures into known antineoplastic agents, including podophyllotoxin, 4'-demethylepipodophyllotoxin-β-D-ethylideneglucoside and 4'-demethylepipodophyllotoxin-β-D-thenylideneglucoside.

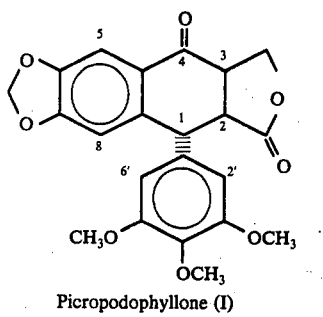

Picropodophyllone (I)

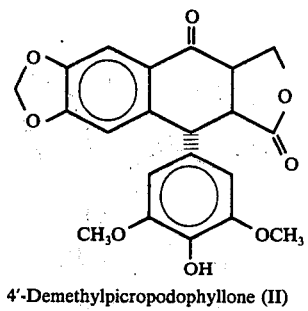

4'-Demethylpicropodophyllone (II)

DESCRIPTION OF THE PRIOR ART

Podophyllotoxin (III), a known lignan lactone isolated from several species of Podophyllum, is a potent cytotoxic agent. Numerous other related compounds having the characteristic aryltetralin ring structure, either naturally occurring or derived from naturally occurring compounds, are known; some of these compounds possess antineoplastic activity while others are useful for conversion to compounds having such activity. Many of these compounds have now been prepared by total synthesis.

In J. Org. Chem., 31, 3224–7 (1966), W. J. Gensler and C. D. Gatsonis describe the results of their investigation into the known facile epimerization of podophyllotoxin (III) into picropodophyllin (IV) under mild base catalysts.

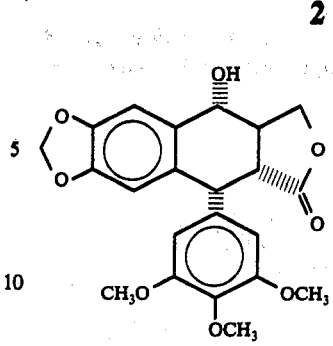

Podophyllotoxin (III)

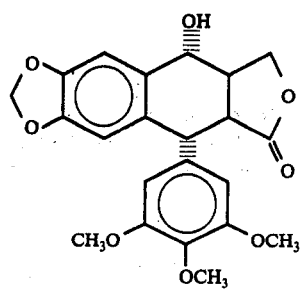

Picropodophyllin (IV)

They report that it is an equilibrium and that the equilibrium mixture contains about 97% picropodophyllin at 31° C., regardless of the direction from which equilibrium is approached. On pages 4004–8 of the same journal these authors describe an elegant procedure for the conversion of picropodophyllin (IV) into podophyllotoxin (III) by preparing the O-tetrahydropyranyl derivative of picropodophyllin, converting it to the sodium enolate by treatment with triphenylmethylsodium, and quenching the enolate with excess acetic acid. This reaction gave the desired podophyllotoxin (III) in 38% yield, with a 51% recovery of picropodophyllin (IV).

In J. Am. Chem. Soc., 82, 1714–1727 (1960), W. J. Gensler, et al. report the total synthesis of picropodophyllin (IV) by a lengthy procedure which is completely different than that described herein. Those authors required nine steps to go from the intermediate trans-1-(3',4',5'-trimethoxyphenyl)-6,7-methylenedioxy-4-tetralone-2-carboxylic acid (their Xa; our V) to picropodophyllin (their XXIII; our IV), while the same conversion is accomplished in three steps in the process described herein.

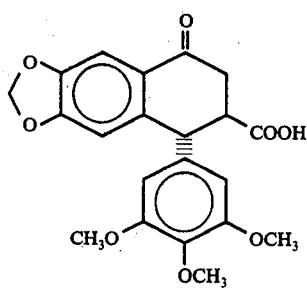

In J. Am. Chem. Soc., 82, 6074–6081 (1960), W. J. Gensler, et al. describe the interconversion of various compounds closely related to podophyllotoxin (III), including the zinc borohydride reduction of picropodophyllone (I) to picropodophyllin (IV).

In J. Am. Chem. Soc., 75, 4681-4 (1953), K. N. Campbell, et al. disclose inter alia the following reaction:

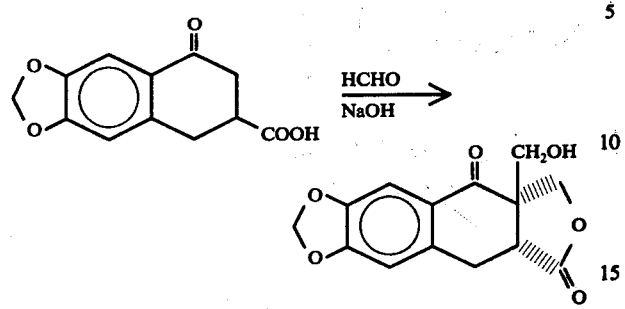

In the Indian Journal of Chemistry, 13, 882-5 (1975), A. P. Wagh and A. B. Kulkarni disclose the preparation of the compound of the formula:

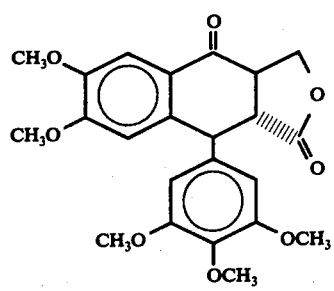

by cyclization of (with acetic anhydride in pyridine) or pyrolysis of (180° for 4 hours) the compound of the formula

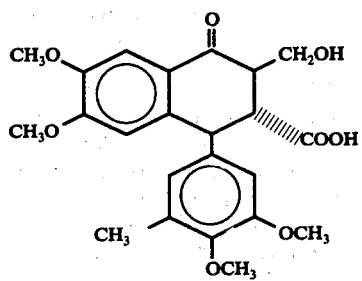

The use of thallium (III) trifluoroacetate (TTFA) for intramolecular oxidative phenol coupling, with conversion of the phenolic groups to oxo (carbonyl) groups, are known for example from J. Am. Chem. Soc., 95, 612-3 (1973). The authors report reactions such as the following (the nitrogen atom having been protected by a blocking group):

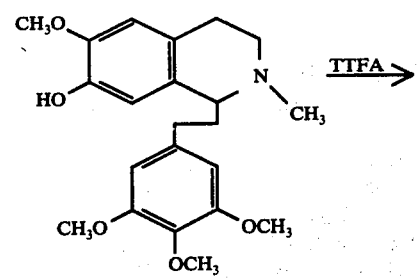

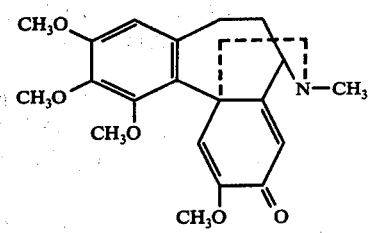

In Helv. Chim. Acta, 52, 944-7 (1969), M. Kuhn et al. report the preparation of 4'-demethylepipodophyllotoxin (their III; our VI) from podophyllotoxin (III) via intermediates 4-bromo-4-deoxyepipodophyllotoxin (their VI; our VII) and 4-bromo-4-deoxy-4'-demethylepipodophyllotoxin (their VII; our VIII).

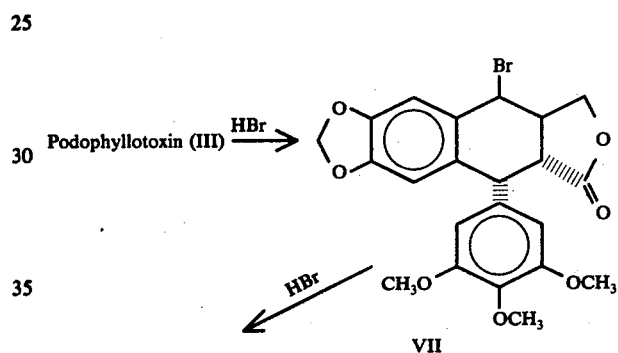

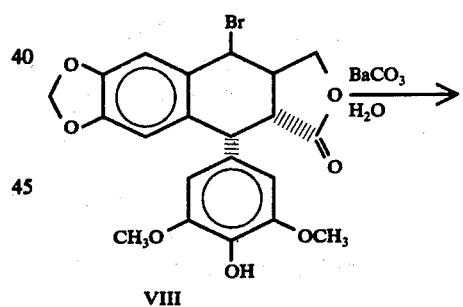

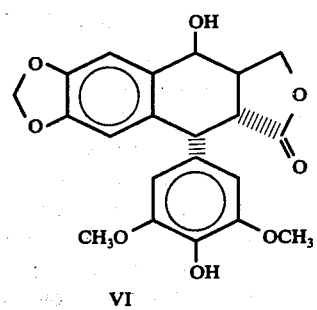

The authors also prepared VI from 4'-demethylpodophyllotoxin (IX) via the intermediate 4-chloro-4-deoxy-4'-demethylepipodophyllotoxin (X).

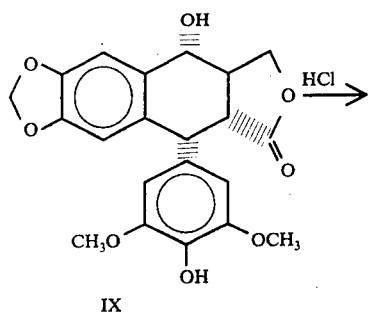

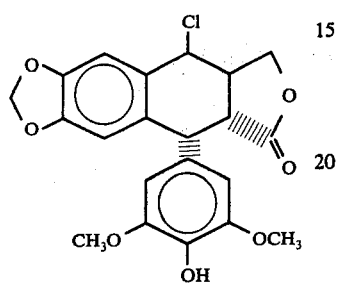

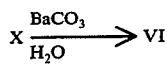

U.S. Pat. 3,524,844 discloses 4'-demethylepipodophyllotoxin-β-D-(substituted)glucosides of the formula

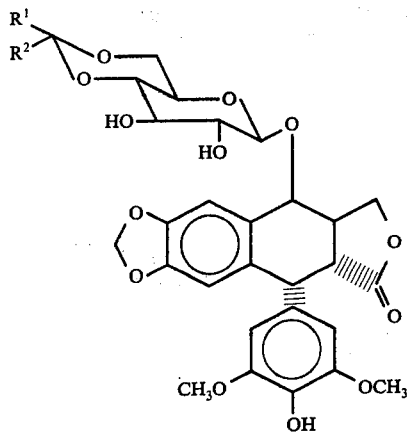

wherein, inter alia, $R^1$ is hydrogen and $R^2$ is an alkyl or 2-thienyl moiety. The compounds are prepared by reacting 4'-carbobenzoxy-4'-demethylepipodophyllotoxin (4'-Cbz-VI) with α-acetobromoglucose or by reacting 4'-carbobenzoxy-4'-demethylpodophyllotoxin (4'-Cbz-IX) with 2,3,4,6-tetra-O-acetyl-β-D-glucose, each of which reactions produces tetra-O-acetyl-4'-carbobenzoxy-4'-demethylepipodophyllotoxin-β-D-glucoside. After removal of the acetoxy groups by alcoholysis and removal of the carbobenzoxy group by hydrogenolysis, the resulting 4'-demethylepipodophyllotoxin-β-D-glucoside (XI)

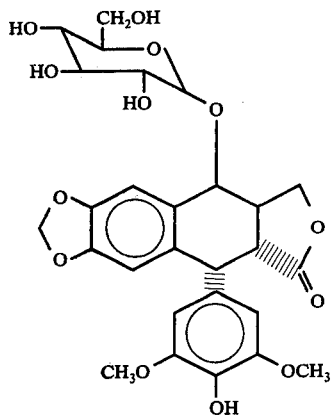

is reacted with a compound of the formula

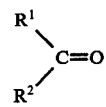

wherein $R^1$ and $R^2$ are, inter alia, as defined above. The 4'-demethylepipodophyllotoxin-β-D-(substituted)-glucosides are antineoplastic agents.

COMPLETE DISCLOSURE

This invention relates to new and efficient total syntheses of (±)-picropodophyllone (I) and (±)-4'-demethylpicropodophyllone (II) which are readily converted by known procedures into known antineoplastic agents, including podophyllotoxin (III), 4'-demethylepipodophyllotoxin-β-D-ethylideneglucoside (XII-a; $R^1$ = methyl) and 4'-demethylepipodophyllotoxin-β-D-thenylideneglucoside (XII-b; $R^1$ = 2-thienyl).

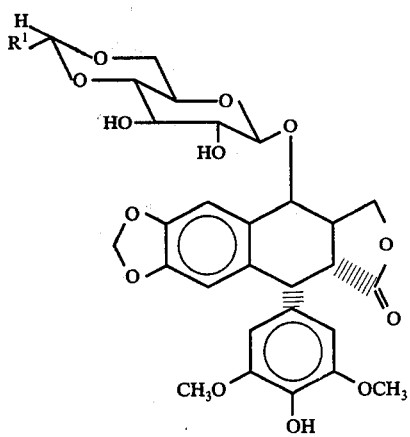

XII-a $R^1$ = methyl
XII-b $R^1$ = 2-thienyl

Compounds I and II are prepared by total synthesis starting with a phenol of Formula XIII

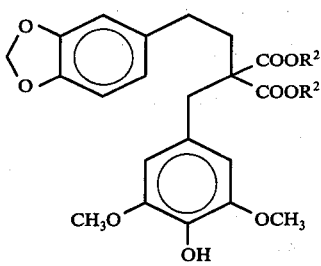

XIII in which R² is (lower)alkyl. Compound XIII is treated with thallium (III) trifluoroacetate (TTFA) to produce a compound of Formula XIV-a

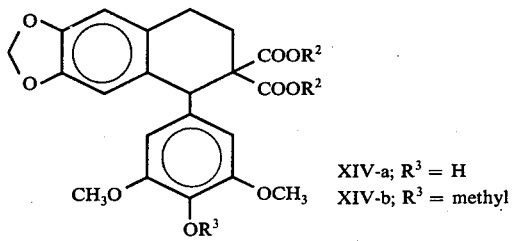

XIV-a; R³ = H
XIV-b; R³ = methyl in which R² is as defined above and R³ is hydrogen. Compound XIV-a can be methylated with dimethyl sulfate to produce a compound of Formula XIV-b in which R³ is methyl. Compounds XIV-a and XIV-b may then individually be subjected to the following reaction steps to produce 4'-demethylpicropodophyllone (II) or picropodophyllone (I), respectively. The following reaction scheme illustrates the use of compound XIV-b to produce picropodophyllone (I); it will be understood that the use of compound XIV-a in this reaction scheme will produce 4'-demethylpicropodophyllone (II).

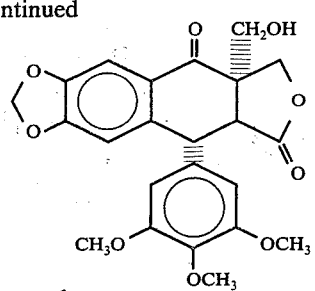

picropodophyllone (I)

XVI

Picropodophyllone (I) produced according to the above reaction scheme may be converted to picropodophyllin (IV) by zinc borohydride reduction, as described by W. J. Gensler et al. in J. Am. Chem. Soc., 82, 6074–6081 (1960). The picropodophyllin (IV) thus produced may be converted to the known antineoplastic agent, podophyllotoxin (III) by the Gensler enolate quenching procedure, as described in J. Org. Chem., 31, 3224–7 (1966).

When 4'-demethylpicropodophyllone (II) is produced by the above reaction scheme (by starting with compound XIV-a), it may be converted to 4'-demethylpodophyllotoxin (IX) by the known procedures described in the preceding paragraph. The resulting 4'-demethylpodophyllotoxin (IX) may then be converted to the known antineoplastic agents 4'-demethylepipodophyllotoxin-β-D-ethylideneglucoside (XII-a) or 4'-demethylepipodophyllotoxin-β-D-thenylideneglucoside (XII-b) by the procedures described in U.S. Pat. No. 3,524,844.

The ring closure of compound XIII (R²=ethyl) with TTFA under normal reaction conditions (e.g. 1.3–1.5 equivalents of TTFA, 1,2-dichloroethane, 84°, 30 min) followed by sodium bisulfite reduction gives a 52% yield of a mixture containing about 17% of phenol XIV-a and about 83% of catechol XVII.

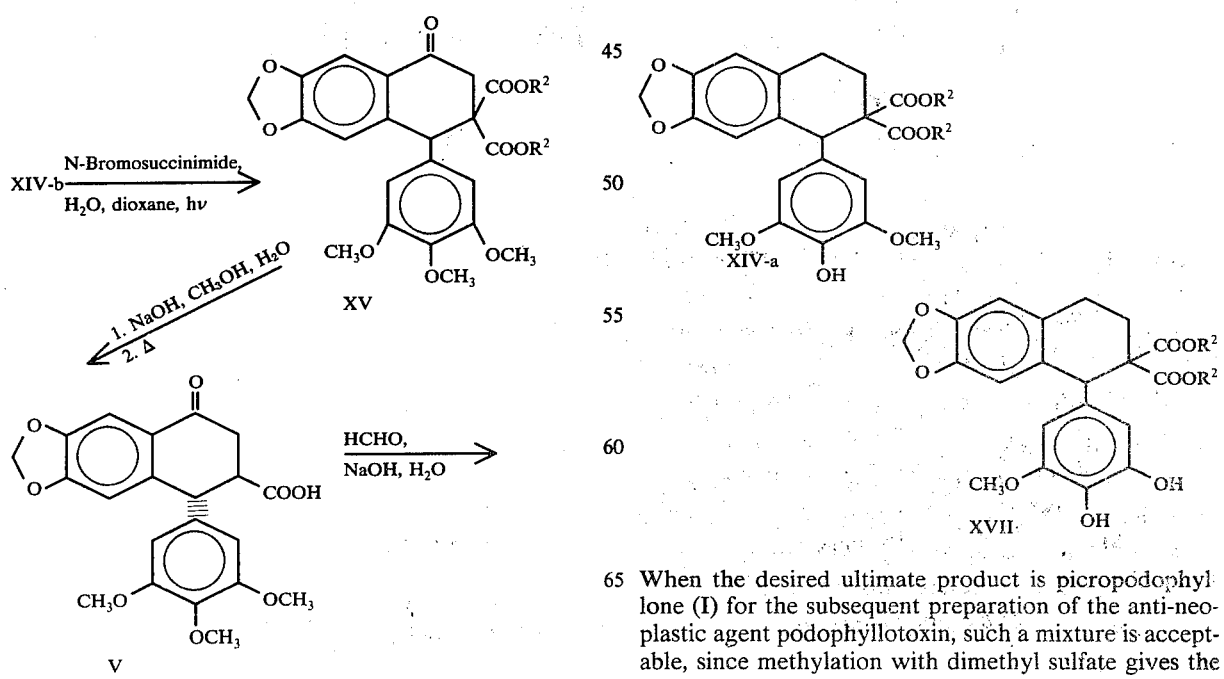

When the desired ultimate product is picropodophyllone (I) for the subsequent preparation of the anti-neoplastic agent podophyllotoxin, such a mixture is acceptable, since methylation with dimethyl sulfate gives the desired XIV-b as the sole product. However, when the desired ultimate product is 4′-demethylpicropodophyllone (II) for subsequent preparation of 4′-demethylepipodophyllotoxin-β-D-(substituted)glucosides such as XII-a and XII-b, such a mixture of phenol XIV-a and catechol XVII is unacceptable. We have surprisingly found that the oxidative ring closure of XIII with TTFA in the presence of an excess of a Lewis acid gives good yields of the phenol XIV-a as the sole product. The reaction is conducted in an inert organic solvent such as methylene chloride, chloroform, carbon tetrachloride, 1,2-dichloroethane, or the like, utilizing from about 1 to about 2 moles (and preferably from about 1 to about 1.5 moles) of TTFA per mole of compound XIII, in the presence of an excess of a Lewis acid such as $AlCl_3$, $ZnCl_2$, boron trifluoride etherate, or the like (but preferably boron trifluoride etherate). Up to about 10 moles of Lewis acid are used per mole of TTFA; even higher amounts may be used, but do not improve the yield of desired product. The reaction is conducted at a temperature of from about 10° to about 35° (and most conveniently at room temperature) for up to about 24 hours or more (and preferably from about 4 to about 18 hours). At the completion of the reaction, a mild reducing agent is added to reduce excess TTFA. Such mild reducing agents are known to those skilled in the art and include, for example, sodium bisulfite, potassium bisulfite, sodium metabisulfite, potassium metabisulfite, sodium thiosulfate, potassium thiosulfate, sulfur dioxide, stannous chloride, zinc metal, KI NaI, LiI and the like. If KI, NaI or LiI are used to reduce the excess TTFA it is desirable to subsequently add a sufficient amount of a different mild reducing agent, e.g. sodium metabisulfite, to reduce the free iodine which is formed.

As used herein and in the claims, the term "(lower)alkyl" means a straight or branched chain alkyl group containing from 1 to 6 carbon atoms. All temperatures are given in ° C. "Florisil" is a registered trademark of the Floridin Company for magnesia-silica gel (magnesium silicate) used in chromatography.

PREPARATION OF STARTING MATERIAL XIII ($R^2$=ETHYL)

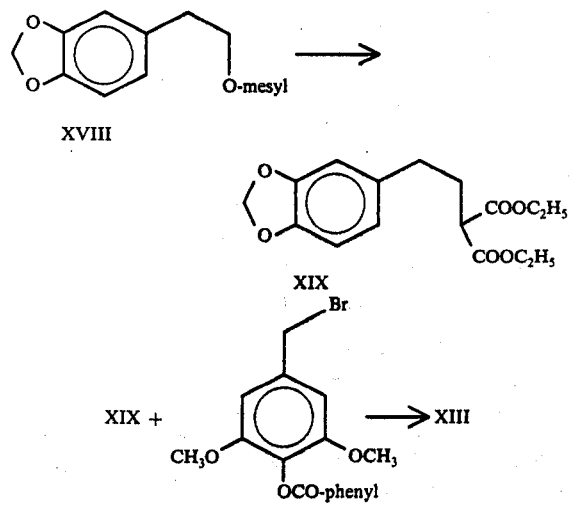

Ethyl 2-Carbethoxy-4-(3,4-methylenedioxyphenyl)butyrate (XIX)

A 50% dispersion of NaH in mineral oil (1.92 g, 40 mmole) was added to a flamed round-bottom flask and the mineral oil was removed by washing with hexane. Benzene (50 ml) was added and the contents of the flask were placed under nitrogen. Diethyl malonate (7.05 g, 44 mmole) was added dropwise with hydrogen evolution. After the gas evolution had ceased, the reaction was heated just below reflux and then 2-(3,4-methylenedioxyphenyl)ethyl mesylate (XVIII) (4.90 g, 20 mmole) in benzene (30 ml) was added all at once via syringe. The reaction was refluxed with stirring for 14 hrs and then cooled. The reaction mixture was transferred to a separatory funnel and washed with water and saturated brine, and dried over magnesium sulfate. Filtration and evaporation of the solvent left an oil from which excess diethyl malonate was removed by pumping at 1 mm Hg and 70°. This left 5.8 g (94%) of slightly crude product (XIX) which was sufficiently pure for the next reaction but could be purified by distillation at 1 mm Hg, b.p. 163°–171°.

ir ($CHCl_3$, $cm^{-1}$): 1730 nmr ($CDCl_3$, 100 MHz): δ6.66 (multiplet, 3H), 5.89 (singlet, 2H), 4.19 (quartet, J = 7, 4H), 3.31 (triplet, J = 7, 1H), 2.59 (triplet, J = 7, 2H), 2.19 (multiplet, 2H)

ms (70 eV): m/e 308(M+), 217, 189, 148.

Ethyl 2-Carbethoxy-2-(3,5-dimethoxy-4-hydroxybenzyl)-4-(3,4-methylenedioxyphenyl)butyrate (XIII)

A 50% dispersion of NaH in mineral oil (40 mg, 0.8 mmole of NaH) was added to a flamed round-bottom flask and the mineral oil was removed by washing with hexane. Compound XIX (67.8 mg, 0.22 mmole) in benzene (1 ml) was added, followed by the careful addition of water (3.6 μl, 0.20 mmole). Then, 4-benzoyloxy-3,5-dimethoxybenzene bromide (XX) (70.2 mg, 0.20 mmole) in dimethylformamide (0.3 ml) was added and the reaction was stirred for 3 hrs at 50°. It was then carefully poured into 4% HCl and extracted with ether. The ether layer was washed with saturated sodium bicarbonate, water and saturated brine, and dried over sodium sulfate. Filtration and evaporation of the solvent left 77.4 mg (82%) of the title product (XIII) as a clear oil. Trituration with ether gave a fluffy white solid which was recrystallized from methanol, m.p. 80°–81°.

ir ($CHCl_3$, $cm^{-1}$): 3530, 1730 nmr ($CDCl_3$, 100 MHz): δ6.56 (multiplet, 3H), 6.29 (singlet, 2H), 5.83 (singlet, 2H), 5.40 (broad singlet, 1H), 4.15 (quartet, J = 7, 4H), 3.77 (singlet, 6H), 3.19 (singlet 2H), 2.50 (multiplet, 2H), 2.04 (multiplet, 2H), 1.21 (triplet, J = 7, 6H)

ms (70 eV): m/e 474 (M+), 460, 429, 383, 326, 280

Anal. Calc'd for $C_{25}H_{30}O_9$: C, 63.27; H, 6.83. Found: C, 63.52; H, 6.37.

EXAMPLE 1

2,2-Dicarbethoxy-1-(4′-hydroxy-3′,5′-dimethoxyphenyl)-6,7-methylenedioxytetralin (XIV-a; $R^2$=ethyl)

A suspension of thallium (III) trifluoroacetate (733 mg 1.35 mmoles) in dichloromethane (12 ml) was cooled in an ice bath, under nitrogen. Ethyl 2-carbethoxy-2-(3,5-dimethoxy-4-hydroxybenzyl)-4-(3,4-methylenedioxyphenyl)butyrate (XIII; $R^2$ = ethyl) (474 mg, 1.00 mmoles) and boron trifluoride etherate (1.45 ml, 11.49 mmoles) were added quickly, the mixture was allowed to come to room temperature, and stirred overnight. Excess aqueous potassium iodide was added, the mixture was stirred for 30 min., made basic with sodium carbonate, and sodium metabisulphite (300 mg, 1.58 mmoles) was added. The thallium (I) iodide was removed by filtration, and washed thoroughly with chloroform. Ethyl acetate was added to the combined filtrate and washings, the organic phase was dried (brine, sodium sulphate) and the solvents were removed. An ether solution of the resulting brown solid (430 mg) was percolated through Florisil. Removal of the solvent gave a yellow oil which deposited fine white needles (260 mg, 55%) on trituration with ether. Crystallization from ether gave 2,2-dicarbethoxy-1-(4'-hydroxy-3',5'-dimethoxyphenyl)-6,7-methylenedioxytetralin as white needles m.p. 147°–148°.

nmr (CDCl$_3$, 100 MHz): $\delta$6.52 (singlet, 1H) 6.40 (singlet, 1H) 6.24 (singlet, 2H) 5.84 (singlet, 2H) 5.36 (broad, 1H, OH) 4.72 (singlet, 1H) 4.28–3.88 (Two overlapping quartets, 4H) 3.76 (singlet, 6H) 2.86–2.28 (Multiplet, 4H) 1.16 (quartet, two overlapping triplets, 6H)

ms (70 eV): 472 (M+), 455, 398.

EXAMPLE 2

2,2-Dicarbethoxy-1-(3',4',5'-trimethoxyphenyl)-6,7-methylenedioxytetralin (XIV-b; R$^2$=ethyl)

Thallium (III) trifluoroacetate (6.5 g; 11.96 mmoles) was suspended in 1,2-dichloroethane (75 ml) and heated to reflux under nitrogen. Ethyl 2-carbethoxy-2-(3,5-dimethoxy-4-hydroxybenzyl)-4-(3,4-methylenedioxyphenyl)butyrate (XIII) (4.2 g, 8.86 mmoles) in 5 ml of 1,2-dichloroethane was then added and the reaction mixture became deep red. Refluxing was continued for 30 min. The solution was cooled, poured into saturated sodium bisulfite, and turned yellow. The aqueous layer was extracted with ethyl acetate and the organic layer was washed with saturated sodium bicarbonate, water, and saturated brine, and was dried over sodium sulfate. Filtration and evaporation gave a brown oil which was dissolved in 50 ml of acetone. To this was added 3 ml of dimethyl sulfate and 18 g of anhydrous potassium carbonate. This mixture was refluxed overnight, cooled and poured into water. The aqueous phase was extracted with chloroform and the chloroform was washed with water and saturated brine, and dried over sodium sulfate. Filtration and evaporation gave a brown oil which, when triturated with methanol, gave 1.8 g of the title product (XIV-b; R$^2$ = ethyl). Chromatography of the methanol residue on silica gel (1/1 ether/cyclohexane) gave an additional 0.5 g (55% total yield). Recrystallization from methanol gave a white solid (mp 149°–152°).

ir (CHCl$_3$, cm$^{-1}$): 1730 nmr (CDCl$_3$, 100 MHz-PFT): $\delta$6.54 (singlet, 1H), 6.43 (singlet, 1H), 6.23 (singlet, 2H), 5.86 (doublet, J = 1.2, 2H), 4.76 (singlet, 1H), 4.08 (two overlapping quartets, 4H), 3.79 (singlet, 3H), 3.74 (singlet, 6H), 2.84–2.30 (multiplet, 4H), 1.21 (triplet, J = 7.2, 3H), 1.12 (triplet, J = 7.3, 3H)

ms (70 e/V): m/e 486 (M+), 468, 411, 367

Anal. Calc'd for C$_{26}$H$_{30}$O$_9$: C, 64.18; H, 6.23. Found: C, 64.06; H, 6.24.

EXAMPLE 3

2,2-Dicarbethoxy-1-(3',4',5'-trimethoxyphenyl)-6,7-methylenedioxy-4-tetralone (XV; R$^2$=ethyl)

In a small Pyrex tube equipped with a spin bar was added 50 mg of 2,2-dicarbethoxy-1-(3',4',5'-trimethoxyphenyl)-6,7-methylenedioxytetralin (XIV-b; R$^2$ = ethyl) and 72 mg (4.0 eq) of N-bromosuccinimide (recrystallized from water). Dioxane (2 ml) was distilled in (from (Na/benzophenone), and the tube was sealed and placed under nitrogen. The mixture was irradiated for 2 min with a sunlamp while cooling with a cold water stream. Water ($+\mu$l) was then syringed in and irradiation and cooling was maintained for 18 to 20 min. The reaction mixture was then poured into saturated sodium bisulfite and extracted three times with chloroform. The organic layer was washed twice with 2N sodium hydroxide, twice with water, once with saturated brine, and was dried over sodium sulfate. Filtration and evaporation gave the title product (XV; R$^2$ = ethyl) plus the ring bromination product at C-2' (<10%). One crystallization from methanol gave 46 mg (90%) pure title product, mp 152°–153°.

ir (CHCl$_3$, cm$^{-1}$): 1730, 1690 nmr (CDCl$_3$, 100 MHz): $\delta$7.49 (singlet, 1H), 6.63 (singlet, 1H), 6.24 (singlet, 2H), 5.99 (singlet, 2H), 5.05 (singlet, 1H), ~4.08 (two overlapping quartets, 4H), 3.79 (singlet, 3H), 3.72 (singlet, 6H), 3.24 (singlet, 2H), ~$\delta$1.12 (two overlapping triplets, 6H)

ms (70 eV): m/e 500 (M+), 455, 426, 405, 381

Anal. Calc'd for C$_{26}$H$_{28}$O$_{10}$: C, 62.39; H, 5.64. Found: C, 62.42; H, 5.66

EXAMPLE 4 trans-1-(3',4',5'-trimethoxyphenyl)-6,7-methylenedioxy-4-tetralone-2-carboxylic acid (V)

2,2-Dicarbethoxy-1-(3',4',5'-trimethoxyphenyl)-6,7-methylenedioxy-4-tetralone (XV; R$^2$ = ethyl) (45 mg) was suspended in 10 ml of methanol. Aqueous NaOH (10 ml of 5%) was added and the mixture was refluxed for 3.5 hr. Then the mixture was cooled, diluted with water and washed one time with ether. The base layer was acidified to pH 2 with dilute sulfuric acid and extracted four times with chloroform. The organic layer was washed twice with water and once with saturated brine, and was dried over sodium sulfate. Filtration and evaporation gave a white solid which was heated briefly at 110° C. under nitrogen. Recrystallization of the white solid from methanol gave 24 mg (66%) of the title product, m.p. 221°–223° C.

ir (CHCl$_3$, cm$^{-1}$): 1710, 1685, 3500–3000 broad.

nmr (CDCl$_3$, 100 MHz): $\delta$9.86 (singlet, broad exchangeable, 1H), 7.49 (singlet, 1H), 6.48 (singlet, 1H), 6.30 (singlet, 2H), 6.01 (singlet, 2H), 5.52 (broad doublet, 1H), 4.78 (singlet, 3H), 4.72 (singlet, 6H), 3.30 (multiplet, 1H), 2.80 (broad doublet, 2H)

ms (70 eV): m/e 400(M+), 385, 372, 369, 355.

EXAMPLE 5

($\pm$)-3-Hydroxymethylpicropodophyllone XVI

Trans-1-(3',4',5'-trimethoxyphenyl)-6,7-methylenedioxy-4-tetralone-2-carboxylic acid (V) (46 mg) was dissolved in one ml of 5% sodium hydroxide. Formaldehyde (1.9 ml of 37%) was added and the reaction mixture was stirred for 24 hrs. The solution was then diluted with water and acidified with 5% hydrochloric acid. This was extracted twice with chloroform and twice with ethyl acetate. The combined organic phases were washed twice with water and once with saturated brine, and were dried over sodium sulfate. Filtration, evaporation, chromatography (SiO$_2$, benzene/ethyl acetate, 3/2) and recrystallization (benzene) gave 30 mg (59%) of the title product, m.p. 107°–109°.

ir (CHCl$_3$, cm$^{-1}$): 1780, 1680, 3400 nmr (CDCl$_3$, 100 MHz): δ7.46 (singlet, 1H), 6.68 (singlet, 1H), 6.14 (singlet, 2H), 6.07 (singlet, 2H), 4.77 (broad singlet, 1H), 4.48 (AB quartet, 2H) 3.80 (singlet, 3H), 3.73 (singlet, 6H), 3.73 (overlapping 2H, broad), 3.38 (doublet, 2H).

ms (70 eV): m/e 442 (M+), 412, 411, 397.

EXAMPLE 6

(±)-Picropodophyllone (I)

A. Retroaldol Method

3-Hydroxymethylpicropodophyllone (XVI) (12 mg) dissolved in 2 ml dry xylene in a sealed tube was heated at 190° for 40 hrs. Evaporation of the solvent and chromatography on silica gel (methylene chloride/acetone, 7/1) gave 7.6 mg (70%) of (±)-picropodophyllone.

B. Oxidation Method

A large excess of Jones reagent was added to 24 mg of 3-hydroxymethylpicropodophyllone (XVI) in 3 ml of acetone. After 45 min the reaction was quenched with methanol and poured into chloroform. The organic layer was washed with water and saturated brine, and was dried over sodium sulfate. Filtration, evaporation and chromatography as in part A above gave 15.1 mg (71%) of (±)-picropodophyllone.

The synthetic (±)-picropodophyllone was recrystallized from methanol and gave m.p. 198°–199.5°. All spectral data (ir, nmr, ms and uv) and TLC in six solvent systems were identical to a natural sample of (−)-picropodophyllone prepared by equilibration and MnO$_2$ oxidation of natural podophyllotoxin.

ir (CHCl$_3$, cm$^{-1}$): 1765, 1670 nmr (CDCl$_3$, 100 MHz, PFT): δ7.495 (singlet, 1H), 6.684 (singlet, 1H), 6.231 (singlet, 2H), 6.040 (singlet, 2H) 5.3 (broad multiplet), 3.799 (singlet, 3H), 3.750 (singlet, 6H), 3.300 (doublet)

uv (abs. ethanol): $\lambda_{max}$ 320, 278, 237 and 210 nm ms (70 eV): 412 (M.+), 397, 381, 367, 354, 337, 327, 313

We claim:

1. The process for the preparation of a compound of the formula

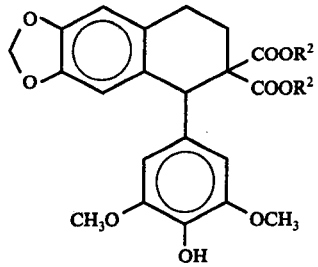

wherein R$^2$ is (lower)alkyl, which comprises treating a compound of the formula in which R$^2$ is as defined above, in an inert organic solvent, with from about 1 to about 2 molar equivalents of thallium (III) trifluoroacetate in the presence of an excess of a Lewis acid, at a temperature of from about 10° to about 35°, reducing the excess thallium (III) trifluoroacetate with a mild reducing agent and recovering the desired product from the reaction mixture.

2. The process of claim 1 wherein the Lewis acid is AlCl$_3$, ZnCl$_2$ or boron trifluoride etherate and is utilized in an amount of from about 1 to about 10 moles per mole of thallium (III) trifluoroacetate.

3. The process of claim 2 wherein the mild reducing agent is (a) sodium bisulfite, potassium bisulfite, sodium metabisulfite, potassium metabisulfite, sodium thiosulfate, potassium thiosulfate, sulfur dioxide, stannous chloride or zinc metal, or (b) KI, NaI or LiI followed by sodium bisulfite, potassium bisulfite, sodium metabisulfite, potassium metabisulfite, sodium thiosulfate, potassium thiosulfate, stannous chloride or zinc metal to reduce free iodine.

4. The process of claim 3 wherein the Lewis acid is boron trifluoride etherate and the mild reducing agent is (a) sodium bisulfite, potassium bisulfite, sodium metabisulfite, potassium metabisulfite, sodium thiosulfate, potassium thiosulfate or sulfur dioxide, or (b) KI, NaI or LiI followed by sodium bisulfite, potassium bisulfite, sodium metabisulfite, potassium metabisulfite, sodium thiosulfate, potassium thiosulfate or sulfur dioxide to reduce free iodine.

5. The process of claim 4 wherein the Lewis acid is boron trifluoride etherate.

6. The process of claim 5 wherein R$^2$ is ethyl.

7. The process of claim 6 wherein the reaction is conducted at about room temperature for a period of from about 4 to about 18 hours.

* * * * *